United States Patent [19]
Anawis et al.

[11] Patent Number: 4,782,023
[45] Date of Patent: Nov. 1, 1988

[54] STABILIZED HORSERADISH PEROXIDASE CONJUGATE COMPOSITION

[75] Inventors: Mark A. Anawis, Gurnee; Roger E. Lindberg, Libertyville, both of Ill.

[73] Assignee: Abbott Laboratories, Abbott Park, Ill.

[21] Appl. No.: 775,882

[22] Filed: Sep. 13, 1985

Related U.S. Application Data

[63] Continuation of Ser. No. 576,824, Feb. 3, 1984, abandoned.

[51] Int. Cl.$^4$ .......................... C12N 9/96; C12N 9/08; G01N 13/00
[52] U.S. Cl. .................................. 435/188; 435/192; 435/28; 436/15; 436/18
[58] Field of Search .................. 435/28, 188, 192; 436/15, 18

[56] References Cited

U.S. PATENT DOCUMENTS 4,325,832 4/1982 Louderback ................ 252/408
4,361,652 11/1982 Uemura et al. ............. 435/188

FOREIGN PATENT DOCUMENTS 2067572 7/1981 United Kingdom ............. 424/91

OTHER PUBLICATIONS

Kutuzova et al., Chem. Abst., vol. 94(15) No. 116870d, 1980, "Stabilization of Horseradish Peroxidase in the Presence of Calcium Ions and by Acetylation of the Enzyme".

Eriksson et al., Chem. Abst. vol. 90(17) No. 134538y, 1979, "A Method for the Preparation of Heavy Atom Derivatives of Yeast Cytochrome C Peroxidase".

Middleton, Chem. Abst., vol. 69(25) No. 103698v, 1960, "Preparation and Investigation of a Stabilized Glucose Oxidase Peroxidase Reagent . . . and Polyethylene Glycol".

Primary Examiner—Thomas G. Wiseman
Assistant Examiner—Robin L. Teskin
Attorney, Agent, or Firm—Robert W. Stevenson; Martin L. Katz

[57] ABSTRACT

An enzyme conjugate composition comprising an enzyme conjugate, a calcium salt and a polyethylene glycol is disclosed. The enzyme conjugate composition is effectively stabilized by the presence of the calcium salt and the polyethylene glycol.

12 Claims, No Drawings

STABILIZED HORSERADISH PEROXIDASE CONJUGATE COMPOSITION

This is a continuation of application Ser. No. 576,824 filed Feb. 3, 1984.

BACKGROUND OF THE INVENTION

1. Technical Field

The present invention relates to reagents for use in enzyme immunoassay (EIA) procedures.

2. Background Art

In immunoassay procedures typically used in clinical diagnostics, antibodies and antigens are conjugated with enzymes, forming enzyme conjugates, to detect the presence and/or amount of various analytes, i.e., antigens or antibodies in test samples prepared from biological fluids such as plasma, serum, spinal fluid or amniotic fluid. The presence and/or the amount of the analyte can be determined by measuring the formation of resulting antibody-antigen-enzyme complexes. The conjugated enzymes can, for example, activate suitable indicator substances, such as dyes which produce a colorimetric change resulting from interaction of the enzyme and the dye. The colorimetric change can be determined instrumentally by measuring the absorbance of the dye solution, or in some cases, visually, to provide an indication of the analyte. In addition to the use of enzyme conjugated antibodies to detect antigens, such EIAs can also be used to detect the presence of antibodies by reversing the roles of antigens and antibodies in the foregoing procedure.

Two major problems confronting the development of EIAs are sensitivity and reagent stability. Enzyme conjugate compositions used in such assays are usually prepared well in advance of the time the assay procedure is performed. Unfortunately, conventional conjugate compositions used as reagents in EIAs often suffer from substantial instability of their enzyme conjugates which causes their activity to diminish rapidly over time. This instability can be a significant disadvantage because shipping, distribution to customers and storage in inventory usually involve substantial time delays between conjugate preparation and use, and can also subject the preparations to wide temperature variations and other conditions which exacerbate activity degradation. Although current practices entail storage of enzyme conjugates in solutions such as saline and phosphate buffered saline, such solutions, used alone, have been found to provide inadequate stability when solubilized conjugates are subjected to temperature stress or stored for extended lengths of time. Accordingly, an enzyme conjugate composition which exhibits substantially improved stability characteristics by comparison with known compositions would be greatly advantageous.

DEFINITION OF PRECENTAGE

Unless otherwise indicated, the percentages indicated herein are weight/volume.

SUMMARY OF THE INVENTION

The present invention is based upon the discovery of a stabilized enzyme conjugate composition which can be advantageously utilized in enzyme immunoassays. Such a composition according to the invention comprises an enzyme conjugate, a calcium salt and a polyethylene glycol. Preferably, the polyethylene glycol has an average molecular weight of from about 1,000 to about 20,000, and is present in the composition in an amount of from about 0.1% to about 10%.

DETAILED DESCRIPTION OF THE INVENTION

The unexpected discovery that storage of an enzyme conjugate in an enzyme conjugate composition containing a polyethylene glycol and a calcium salt results in substantially enhanced stability, by comparison with storing similar conjugates in a solution containing either calcium or polyethylene glycol alone, or neither of these ingredients, has been studied by the present applicants. In preferred embodiments of the invention described infra, such studies were made in connection with the measurement of human immunoglobulin E (IgE). However, it is to be appreciated that the identity of the enzyme conjugate is not critical to the present invention, and that any enzyme conjugate, such as enzyme-conjugated antibodies to hepatitis A, hepatitis B, carcinoembryonic antigens, or a variety of other antigens, or enzyme-conjugated antigens to antibodies, may be stabilized by application of the principles of the present invention.

Since only a relatively small amount of enzyme conjugate is needed for most immunoassays, the enzyme conjugate composition will usually be present in a aqueous solution of buffer or the like. In order to minimize cost, the amount of enzyme conjugate in the buffer is usually no more than about 1 microgram per milliliter (ug/ml). To maximize effectiveness, however, at least 0.01 ug/ml of the enzyme conjugate is usually present in the solution. The identity of such a buffer is not critical to the present invention, and suitable buffers can be selected from a variety of aqueous solutions known in the art, such as saline solutions, borate solutions and other common buffers, such as phosphate and citrate. When the aqueous solution is a saline solution, it is generally preferred that it comprise about 0.1% to 2% sodium chloride.

A variety of polyethylene glycols which are known in the art are suitable for use in the composition of the present invention. Such polyethylene glycols have been found, in combination with a calcium salt, to impart a high degree of stability to the enzyme conjugate composition of this invention. Polyethylene glycols also have been found to provide the advantage of increasing the sensitivity of immunoassays in which the enzyme conjugate composition may be used, thereby decreasing the amount of enzyme conjugate required to detect the presence of a specific antigen or antibody in a test sample undergoing analysis. For a general discussion of the effects of polyethylene glycol in immunoassays, see "Rapid Solid-Phase Enzyme Immunoassay for Antibodies to Viruses and Other Microbes: Effects of Polyethylene Glycol", Salonen and Vaheri, *Journal of Immunological Methods*, Volume 41, pp. 95–103 (1981).

In a preferred embodiment, the polyethylene glycol utilized in the composition of this invention has an average molecular weight of from about 1,000 to about 20,000. Polyethylene glycols having an average molecular weight of from about 6,000 to about 8,000 are most preferred.

The amount of a polyethylene glycol which is advantageously present in the enzyme conjugate composition of the invention can vary over a wide range. It is preferred, however, that the polyethylene glycol be present in an amount of from about 0.1% to about 10%. In the interest of minimizing expense, however, it is preferred that the polyethylene glycol be present in an amount of from about 1% to about 4% and, most preferably, in an amount of from about 2% to about 3%.

The present invention also requires that a calcium salt be present, together with the polyethylene glycol, in the enzyme conjugate composition of this invention. The calcium salt can be selected from a wide variety of calcium ion-containing compounds known in the art. It is preferred, however, that the salt be chosen so that at least 0.1% thereof is water soluble. Calcium salts, such as calcium halides, for example, $CaCl_2$, $CaBr_2$ and $CaI_2$, and mixtures thereof, and calcium salts of carboxylic acids, such as calcium acetate and calcium propionate, and mixtures thereof, are preferred. Calcium chloride and calcium propionate, and mixtures thereof, are particularly preferred. It is also preferred that the calcium salt be present in an amount of from about 0.05% to about 1%, with amounts of from about 0.1% to about 0.3% being most desirable.

SPECIFIC EMBODIMENTS

Several experiments were conducted to demonstrate various aspects of the invention, and are described in the following Examples. Unless otherwise indicated, the results of these experiments were evaluated using the following procedure.

Initially, all speciments and reagents were brought to room temperature (15°–30° C.). Thereafter, a reaction tray was prepared by pipetting 200 microliters (ul) of phosphate buffered saline solution into each well in the tray, followed by 50 ul of specimen containing IgE standards, control sera, or patient sera with known quantities of human IgE, as indicated for each sample in International units per milliliter (Iu/ml) in the Tables, infra. A single bead with rabbit antibody to human IgE bound to the surface was placed in each well and the tray and beads incubated at 37° C. for 30 minutes. The liquid was then removed from each well and each bead in its well washed 3 times with 4–5 ml solution deionized water. A 200 ul portion of phosphate buffered saline containing horseradish peroxidase conjugated goat antibody ($Ab^{HRP}$) to human IgE, together with either a composition comprising a mixture of a polyethylene glycol and a calcium salt, in experiments conducted according to the invention (Examples 2–5), or, in an experiment conducted not according to the invention but as a control for comparison purposes, without either of these ingredients present (Example 1) or only one ingredient present (Example 6) was added to each well and the tray incubated at 37° C. for 30 minutes. After incubation, the liquid was removed and each bead in its well washed 3 times with 4–5 ml deionized water. Each bead was then transferred to a reaction tube. A solution of a chromogen (e.g., ortho-phenylenediamine) activated by peroxidase (300 ul) was thereafter pipetted into each tube and the tubes incubated at room temperature for 30±2 minutes. Sulfuric acid (1.0 ml, 1N) was added to each tube to stop the action of the enzyme, and the absorbance of the solution was measured at 492 nanometers ($A_{492}$).

COMPARATIVE EXAMPLE 1

An experiment was performed, not in accordance with the invention, but to demonstrate the activity of a conventional enzyme conjugate composition after it was stored at 37° C. for 7 days. A solution was prepared which was composed of approximately 70% of a phosphate buffered saline solution, 29% gamma globulin-free bovine serum, 1% goat serum and 0.1 ug/ml $Ab^{HRP}$ enzyme conjugate. This solution was stored at 37° C. for 7 days. After this time, samples of the solution were tested for activity of the $Ab^{HRP}$ according to the procedure previously outlined. The absorbance of these samples is indicated in the following Table I.

EXAMPLE 2

An experiment was performed in accordance with the invention to demonstrate the improvement in stabilization of enzyme conjugates, even when subjected to storage and temperature stress, when the enzyme conjugate is incorporated in a composition comprising polyethylene glycol and a calcium salt. A solution was prepared using the same ingredients as those indicated in Comparative Example 1, except that the solution additionally contained 0.1% calcium propionate, as well as 3.0% polyethylene glycol with an average molecular weight equal to about 8,000. This solution was stored at 37° C. for 7 days, after which the activity of the $Ab^{HRP}$ was measured according to the procedure outlined supra. The activity of the samples is set forth in the following Table I. As can be seen from a comparison of the results of Comparative Example 1 with the results of Example 2, the $Ab^{HRP}$ composition showed significantly greater activity after being stored for 7 days at 37° C. when it contained a calcium salt and a polyethylene glycol, by comparison with the activity of the enzyme conjugate stored in a composition wherein the calcium salt and polyethylene glycol were absent.

TABLE I

| Example No. | % PEG | % Ca Propionate | $A_{492}$ IgE 0 Iu/ml | IgE 5 Iu/ml | IgE 15 Iu/ml | IgE 100 Iu/ml | IgE 200 Iu/ml |
|---|---|---|---|---|---|---|---|
| 1 | — | — | 0.005 | 0.010 | 0.030 | 0.170 | 0.314 |
| 2 | 3.0 | 0.1 | 0.033 | 0.119 | 0.279 | 1.053 | 1.355 |

EXAMPLES 3, 4 and 5

Several experiments were conducted to demonstrate the present invention wherein the enzyme conjugate composition contains a calcium salt and a polyethylene glycol. In each of Examples 3, 4 and 5, 0.1 ug/ml $Ab^{HRP}$ was stored in a 0.9% saline soluton which also contained 29% newborn calf serum, 1% goat serum, 50 ug/ml Garamycin (an antibiotic), and 3% polyethylene glycol with an average molecular weight of 6,000. In Examples 3, 4 and 5, the solution additionally contained the concentrations of $CaCl_{12}$ indicated in Table II. These solutions were stored at 45° C. for 4 days. After this time the activity of the solutions was determined by the procedure outlined supra. The results of these experiments are indicated in Table II.

COMPARATIVE EXAMPLE 6

An experiment was performed wherein 0.1 ug/ml $Ab^{HRP}$ was stored in the solution used in Examples 3, 4 and 5, except that the enzyme conjugate composition did not contain a calcium salt. This solution was stored at 45° C. for 4 days, after which time its activity was determined according to the procedure outlined supra. The inclusion of both a calcium salt and a polyethylene glycol in the enzyme conjugate composition resulted in significantly greater stabililiy for the enzyme conjugate than when the enzyme conjugate was stored in a buffer which contained polyethylene glycol alone (Table II).

TABLE II

| Example No. | % PEG | % CaCl$_2$ | $A_{492}$ IgE 0 Iu/ml | IgE 5 Iu/ml | IgE 15 Iu/ml | IgE 100 Iu/ml | IgE 200 Iu/ml |
|---|---|---|---|---|---|---|---|
| 3 | 3 | 0.2 | 0.045 | 0.132 | 0.291 | 1.124 | 1.370 |
| 4 | 3 | 0.3 | 0.047 | 0.131 | 0.278 | 1.021 | 1.357 |
| 5 | 3 | 0.5 | 0.028 | 0.123 | 0.289 | 0.986 | 1.138 |
| 6 | 3 | — | 0.004 | 0.050 | 0.123 | 0.545 | 0.717 |

COMPARATIVE EXAMPLE 7

An experiment was performed to demonstrate the effect of a calcium salt in the enzyme conjugate composition. Comparative Example 7 was carried out using the same solution as Example 2 except that the solution contained 0.1% by weight propionic acid instead of calcium propionate. Samples taken from this composition were stored at 37° C. for 7 days, after which time the activity of these samples was tested using the procedure outlined previously. The results of these tests are indicated in the following Table III, wherein the results of Example 2 are also reproduced for comparison. As shown, the solution which contained calcium propionate rather than propionic acid showed substantially greater stability by comparison with the solution of Comparative Example 7 which did not contain the calcium salt.

TABLE III

| Example No. | % PEG | % Priopionic Acid | % Ca Propionate | $A_{492}$ IgE 0 Iu/ml | IgE 5 Iu/ml | IgE 15 Iu/ml | IgE 100 Iu/ml | IgE 200 Iu/ml |
|---|---|---|---|---|---|---|---|---|
| 7 | 3 | 0.1 | — | 0.021 | 0.092 | 0.238 | 0.842 | 1.132 |
| 2 | 3 | — | 0.1 | 0.033 | 0.119 | 0.279 | 1.053 | 1.355 |

It will be understood that various changes and modifications may be made in the enzyme conjugate composition of the invention as herein specifically described without departing from the spirit and scope of the invention, which is defined solely in the following claims.

What is claimed is:

1. A stabilized enzyme conjugate composition, comprising a horseradish peroxidase conjugate, and a stabilizing effective amount of a calcium salt and a polyethylene glycol.

2. The composition of claim 1 wherein the polyethylene glycol has an average molecular weight of from about 1,000 to about 20,000.

3. The composition of claim 2 wherein the polyethylene glycol has an average molecular weight of from about 6,000 to about 8,000.

4. The composition of claim 1 wherein at least 0.1% of the calcium salt is water soluble.

5. The composition of claim 1 wherein the calcium salt is calcium chloride.

6. The composition of claim 1 wherein the calcium salt is calcium propionate.

7. The composition of claim 1 wherein the calcium salt is present in an amount of from about 0.05% to about 1%.

8. The composition of claim 7 wherein the calcium salt is present in an amount of from about 0.1% to about 0.3%.

9. The composition of claim 1 wherein the polyethylene, glycol is present in an amount of from about 0.1% to about 10%.

10. The composition of claim 9 wherein the polyethylene glycol is present in an amount of from about 1% to about 4%.

11. The composition of claim 1 wherein the enzyme conjugate is present in an amount of from about 0.01 to about 1.0 ug/ml.

12. An enzyme conjugate composition containing a horseradish peroxidase conjugate, about 0.05% to about 1% of a calcium salt and about 0.1% to about 10% of a polyethylene glycol with an average molecular weight of from about 1,000 to about 20,000.

* * * * *